United States Patent [19]

Suzuki et al.

[11] Patent Number: 5,155,115
[45] Date of Patent: Oct. 13, 1992

[54] THIENOPYRIDINE DERIVATIVES

[75] Inventors: Fumio Suzuki, Mishima; Yoshikazu Miwa, Shizuoka; Hiroaki Hayashi, Shizuoka; Akio Ishii, Shizuoka; Shunji Ichikawa, Shizuoka; Ichiro Miki, Shizuoka, all of Japan

[73] Assignee: Kyowa Hakko Kogyo Co., Ltd., Tokyo, Japan

[21] Appl. No.: 847,670

[22] Filed: Mar. 4, 1992

[30] Foreign Application Priority Data

Mar. 12, 1991 [JP] Japan .................... 3-46266

[51] Int. Cl.$^5$ ........................... C07D 513/04
[52] U.S. Cl. ..................... 514/301; 546/114
[58] Field of Search .................. 546/114; 514/301

[56] References Cited

U.S. PATENT DOCUMENTS 3,903,095  9/1975  Shen et al. ............... 546/114
3,951,989  4/1976  Kuwada et al. ............ 546/114

OTHER PUBLICATIONS

Fozard, TIPS, vol. 8 (1987) 501:6.
Miner et al., Br. J. Cancer, vol. 56 (1987) 159:62.
Barker et al., J. Chem. Res. (1985) 214:5.
Barker et al., J. Chem. Res. (1986) 122:3.
Barker et al., J. Chem. Res. (1980) 6:7.
Barker et al., J. Chem. Res. (1984) 84:5.

*Primary Examiner*—C. Warren Ivy
*Assistant Examiner*—Zinna Northington Davis
*Attorney, Agent, or Firm*—Fitzpatrick, Cella, Harper & Scinto

[57] ABSTRACT

Disclosed is a thienopyridine derivative represented by formula (I):

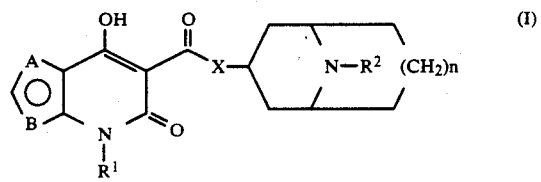

wherein one of A and B represents —S— and the other represents —CH=; X represents —O— or —NH—; $R^1$ represents hydrogen or lower alkyl; $R^2$ represents lower alkyl; and n represents 0 or 1; or a pharmaceutically acceptable salt thereof.

The thienopyridine derivative is useful as anti-emetics and suppressant of migraine.

5 Claims, No Drawings

THIENOPYRIDINE DERIVATIVES

BACKGROUND OF THE INVENTION

The present invention relates to thienopyridine derivatives. The thienopyridine derivatives show a serotonin-3 (hereinafter referred to as 5-HT$_3$) antagonizing activity and are useful as medicinal agents.

It is known that 5-HT$_3$ antagonists exhibit an antiemetic activity, an antianxious activity, a suppressing activity of mental disorders, a suppressing activity of migraine, etc. [Trends in Pharmacological Sciences, 8, 501 (1987)]. Particularly, 5-HT$_3$ antagonists are effective against carcinostatic agent-induced vomiting, which has not been cured by dopamine antagonists. The 5-HT$_3$ antagonists are thus expected to be antiemetics of new type [Br. J. Cancer, 56, 159 (1987)].

As thienopyridine derivatives, compounds (A) having the 4-hydroxythieno[2,3-b]pyridin-6-one skeleton are described in J. Chem. Res. (S), 214 (1985) and J. Chem. Res. (S), 122 (1986):

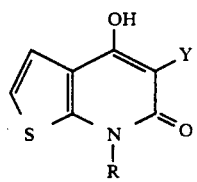

wherein R represents hydrogen or methyl and Y represents hydrogen or ethoxycarbonyl.

Furthermore, compounds (B) having the 7-hydroxythieno[3,2-b]pyridin-5-one skeleton are described in J. Chem. Res. (S), 6 (1980) and J. Chem. Res. (S), 84 (1984):

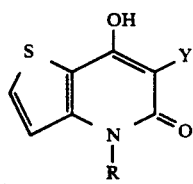

wherein R represents hydrogen or methyl and Y represents hydrogen, ethoxycarbonyl, nitrile, acetyl or the like.

In compounds (A) and (B), their pharmacological activities are unknown.

SUMMARY OF THE INVENTION

The present invention relates to thienopyridine derivatives [hereinafter referred to as Compound (I)] represented by formula (I):

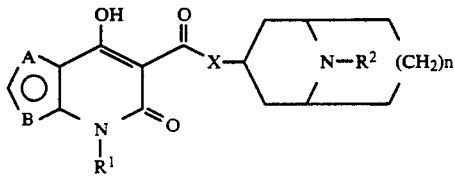

wherein one of A and B represents —S—, and the other represents —CH=; X represents —O— or —NH—; R$^1$ represents hydrogen or lower alkyl; R$^2$ represents lower alkyl; and n represents 0 or 1; or a pharmaceutically acceptable salt thereof.

DETAILED DESCRIPTION OF THE INVENTION

In the definition of each group in formula (I), the lower alkyl means straight or branched alkyl having 1 to 6 carbon atoms such as methyl, ethyl, propyl, isopropyl, butyl, isobutyl, sec-butyl, tert-butyl, pentyl, neopentyl, hexyl, etc.

The pharmaceutically acceptable salts of Compound (I) include acid addition salts, metal salts, etc. Examples of the acid addition salts are inorganic acid salts such as hydrochlorides, sulfates, phosphates, etc.; organic acid salts such as acetates, maleates, fumarates, tartarates, citrates, etc. Examples of the metal salts include salts of alkali metals such as sodium, potassium, etc., salts of alkaline earth metals such as magnesium, calcium, etc.; aluminum salts, zinc salts and the like.

Next, a process for preparing Compound (I) is described.

In the process shown below, in cases where the defined group(s) change under the conditions or are inappropriate for the practice of the process, the process can be easily operated by applying thereto means conventionally used in organic synthetic chemistry, for example, protection of functional groups, removal of protective groups, etc.

Compound (I) may be obtained by reacting Compound (II) represented by formula (II):

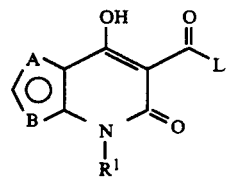

wherein L represents a leaving group; and A, B and R$^1$ have the same significance as described above, with Compound (III) represented by formula (III):

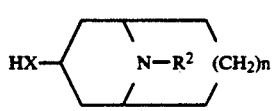

wherein X has the same significance as described above, preferably in the presence of a base.

Herein as the leaving group denoted by L, halogen such as chlorine, bromine, iodine, etc.; alkoxy such as methoxy, ethoxy, etc.; aryloxy such as phenoxy, etc.; alkanoyloxy such as propionyloxy, etc.; aroyloxy such as benzoyloxy, etc. are used.

As the base, alkali metal bicarbonates such as sodium bicarbonate, potassium bicarbonate, etc.; alkali metal carbonates such as sodium carbonate, potassium carbonate, etc.; alkali metal hydrides such as sodium hydride, etc.; alkali metal alkoxides such as sodium methoxide, sodium ethoxide, etc.; alkali metal salts such as butyl lithium, etc. are used.

As the solvent used in the reaction, any solvent may be used, as long as it is inert to the reaction. For example, ethers such as tetrahydrofuran, dioxane, etc.; amides such as dimethylformamide, dimethylacetamide, etc.; ketones such as acetone, methyl ethyl ketone, etc.;

alcohols such as methanol, ethanol, isopropyl alcohol, etc.; halogenated hydrocarbon such as methylene chloride, chloroform, dichloroethane, etc.; esters such as ethyl acetate, etc.; aromatic hydrocarbons such as benzene, toluene, xylene, etc.; dimethylsulfoxide and the like may be used singly or in combination.

The reaction is carried out at −30° to 200° C., preferably −10° to 100° C. and generally completed in 30 minutes to 20 hours.

The starting compounds (II) can be synthesized by known methods [J. Chem. Res. (S), 6 (1980); ibid., 84 (1984); ibid., 214 (1985); J. Chem. Res. (M), 113 (1980); ibid., 771 (1984); ibid., 2501 (1985)] or by a modified method of these methods.

The desired product in the process described above can be isolated and purified by means of purification conventionally used in organic synthesitic chemistry, for example, by filtration, extraction, washing, drying, concentration, recrystallization, various chromatographies, etc.

Where it is desired to obtain the salts of Compound (I), Compound (I) may be purified as it is in case that Compound (I) is obtained in the form of a salt. In case that Compound (I) is obtained in its free form, Compound (I) is dissolved or suspended in an appropriate solvent, and an appropriate acid or base is added to the solution or suspension to form its salt.

Compound (I) and a pharmaceutically acceptable salt thereof may also be present in the form of addition products with water or various solvents. These addition products are also included in the present invention.

Furthermore Compound (I) includes all possible steric isomers and mixtures thereof.

Specific examples of Compound (I) obtained by the process described above are shown in Tables 1 and 2.

TABLE 1

| Compound No. | $R^1$ | $R^2$ | X | n |
|---|---|---|---|---|
| 1 | H | $CH_3$ | NH | 0 |
| 2 | H | $CH_3$ | O | 0 |
| 3 | $(CH_2)_3CH_3$ | $CH_3$ | NH | 0 |
| 4 | $(CH_2)_3CH_3$ | $CH_3$ | O | 0 |

TABLE 2

| Compound No. | $R^1$ | $R^2$ | X | n |
|---|---|---|---|---|
| 5 | $(CH_2)_3CH_3$ | $CH_3$ | NH | 0 |
| 6 | $(CH_2)_3CH_3$ | $CH_3$ | O | 0 |
| 7 | H | $CH_3$ | NH | 0 |
| 8 | H | $CH_3$ | O | 0 |
| 9 | H | $CH_3$ | NH | 1 |

Next, the pharmacological activities and acute toxicity of Compound (I) are described by referring to test examples.

TEST EXAMPLE 1

5-$HT_3$ receptor binding test

Using rat neutroblastoma-glicoma NG108-15 cell membrane fraction, the binding activities of the test compounds to 5-$HT_3$ receptor were examined.

A membrane fraction of NG108-15 cells was prepared according to the method of Neijt et al. [Naunyn-Schmiedeberg's Arch. Pharmacol., 337, 493 (1988)].

The receptor binding test was performed using [$^3$H] quipazine [J. Neurochem., 52, 1787 (1989)], a high affinity ligand to 5-$HT_3$ receptor.

A membrane fraction obtained from $4 \times 10^5$ NG108-15 cells was suspended in 1 ml of 20 mM Tris-hydrochloride buffer (pH 7.5) (hereinafter referred to as Buffer) containing 154 mM sodium chloride. Then, 2 nM [$^3$H] quipazine (2519.7 GBq/mmol; NEN CO.) and various concentrations of the test compound were added to the suspension followed by incubating at 37° C. for 60 minutes. 4 ml of ice-cold Buffer was added to terminate the reaction and then the mixture was filtered through GF/C glass fiber filter (Whatmann Co., Ltd.). The filter was washed 5 times with 2 ml of ice-cold Buffer, and put in a scintillation vial containing 8 ml of Scintisol EX-H (Wako Pure Chemicals, Inc.). Radioactivity on the filter was counted in a liquid scintillation counter (TRI-CARB 2200CA; Packard Co., Ltd.).

An inhibition of the [$^3$H] quipazine binding by the test compound was estimated according to the equation;

$$\text{Inhibition rate (\%)} = \left(1 - \frac{\text{binding in the presence of test compound} - \text{non-specific binding}}{\text{total binding} - \text{non-specific binding}}\right) \times 100$$

"Total binding" is [$^3$H] quipazine-binding in the absence of test compound and "non-specific binding" is [$^3$H] quipazine-binding in the presence of 10 μM MDL7222 5-$HT_3$ antagonist [Naunyn-Schmiedeberg's Arch. Pharmacol., 326, 36 (1984)].

The results are shown in Table 3.

TABLE 3

| Compound No. | Inhibition Rate (%) (concentration) | |
|---|---|---|
| | $10^{-7}$ M | $10^{-8}$ M |
| 1 | 94 | 44 |
| 3 | 101 | 98 |
| 5 | 105 | 100 |
| 7 | 71 | 23 |
| 9 | 69 | 12 |

TEST EXAMPLE 2

Activity Against Cisplatin-induced Vomiting

In one group, 5 to 10 female and male *Suncus murinus* animals weighing 23 to 68 g were used. According to the method of Matsuki et al. [Japan J. Pharmacol., 48, 303 (1988)], each animal was put into a separate metal net cage (width 15 cm × length 21 cm × height 15 cm). One hour after, a test compound or physiological saline (control) was intraperitoneally (i.p.) administered in a dose of 10 μl/g of body weight. Further 30 minutes after administration of the test compound or physiological saline (control), 40 mg/kg of cisplatin was intraperitoneally administered. Taking no account of vomiting caused for 5 minytes after administration of cisplatin, a time period (latency) for the first vomiting and the number of frequencies (episodes) of vomiting caused for the period of 5 to 120 minutes after administration were determined. The latency and the number of frequencies in the test compound administered group were compared with those in the control group. The test of significance was performed by Student's t-test.

The results are shown in Table 4.

TABLE 4

| Compound No. | Dose (mg/kg i.p.) | Number of Vomiting episodes (mean ± S.E.M.) | Latency (min.) (mean ± S.E.M.) |
|---|---|---|---|
| Control | — | 29.2 ± 4.5 | 28.6 ± 6.3 (n = 5) |
| 1 | 1.0 | 9.3 ± 2.2 | 66.0 ± 10.4 (n = 10) |

TEST EXAMPLE 3

Acute Toxicity

A test compound was intraperitoneally and orally administered to dd-Y-strain male mice weighing 20 to 25 g. The minimum lethal dose (MLD) was determined by observing the mortality for 7 days after the administration. The results are shown in Table 5.

TABLE 5

| Compound | MLD (mg/kg) | |
|---|---|---|
| No. | p.o. | i.p. |
| 1 | >300 | >100 |
| 3 | >200 | NT* |
| 4 | >100 | >50 |
| 5 | >300 | >100 |
| 6 | >100 | >100 |
| 8 | >300 | >100 |
| 9 | >300 | >50 |

*NT: not tested

These results suggest that Compound (I) has an excellent 5-HT$_3$ antagonizing activity and low toxicity, and is useful for the treatment of symptoms such as nausea, vomiting which are side effects caused by chemotherapy and radiotherapy of cancer, and for the treatment of anxiety, mental disorders (for example, schizophrenia and mania), for the treatment of migraine and pains, abused drug and chemical dependence, depression, dementia, sensory disorders, etc.

Compound (I) or a pharmaceutically acceptable salt thereof may be used as it is, or in various preparation forms. The pharmaceutical composition of the present invention can be prepared by uniformly mixing an effective amount of Compound (I) or a pharmaceutically acceptable salt thereof as the active ingredient with pharmaceutically acceptable carriers. The pharmaceutical compositions are desirably in a single dose unit suited for oral or parenteral administration.

In preparing the composition suited for oral administration, any pharmaceutically acceptable carrier may be used. Liquid preparations suited for oral administration, for example, a suspension and a syrup can be prepared using water; sugars such as sucrose, sorbitol, fructose, etc.; glycols such as polyethylene glycol, propylene glycol, etc.; oils such as sesame oil, olive oil, soybean oil, etc.; antiseptics such as p-hydroxybenzoic acid ester, etc.; flavors such as strawberry flavor, pepper mint, etc. Further a capsule, a tablet, a powder and a granule can be prepared using an excipient such as lactose, glucose, sucrose, mannitol, etc.; a disintegrator such as starch, sodium alginate, etc.; a lubricant such as magnesium stearate, talc, etc.; a binder such as polyvinyl alcohol, hydroxypropyl cellulose, gelatin, etc.; a surfactant such as a fatty acid ester, etc.; a plasticizer such as glycerine, etc. A tablet and a capsule are most useful single dose unit for oral administration because their administration is easy. An injection solution is prepared with such a carrier as distilled water, a salt solution, a glucose solution, or a mixture of a salt solution and a glucose solution.

Effective dose and number of administration of Compound (I) or a pharmaceutically acceptable salt thereof may vary depending upon modes of administration, age and body weight, conditions, etc. of a patient but it is generally preferred to administer Compound (I) in a dose of 0.01 to 25 mg/kg by dividing into 3 to 4 times.

In addition, Compound (I) may also be administered by inhalation in the form of aerosol, finely divided powders or spray solution. When administered in the form of aerosol, the present compound is dissolved in an appropriate solvent which is pharmaceutically acceptable, for example, ethyl alcohol or in combination with a miscible solvent and the resulting solution may be mixed with a pharmaceutically acceptable propellant Such aerosol composition is filled up in a pressure container equipped with an aerosol valve suited to release a pressurized composition, which is then provided for use. As the aerosol bulb, it is preferred to use a metering bulb predetermined to release an effective dose of the aerosol composition.

The present invention is described by referring to Examples and Reference Examples below.

EXAMPLE 1

Endo-N-(8-methyl-8-azabicyclo[3.2.1]oct-3-yl)-4,5-dihydro-7-hydroxy-5-oxothieno[3,2-b]pyridine-6-carboxamide (Compound 1)

A toluene solution (30 ml) of 1.20 g (5.01 mmols) of ethyl 4,5-dihydro-7-hydroxy-5-oxothieno[3,2-b]pyridine-6-carboxylate [J. Chem. Res. (S), 6 (1980); J. Chem. Res. (M), 113 (1980)] and 0.98 g (6.99 mmols) of 3α-amino-8-methyl-8-azabicylo[3.2.1]octane [J. Am. Chem. Soc., 79, 4194 (1957)]was heated under reflux for 5 hours. After cooling, the mixture was poured into 1 N sodium hydroxide aqueous solution followed by washing twice with chloroform. To the aqueous layer was added 6 N hydrochloric acid aqueous solution to render the layer acidic. The mixture was then extracted 3 times with chloroform containing a small quantity of isopropyl alcohol. After washing the extract with a small quantity of water, the extract was dried over anhydrous sodium sulfate and the solvent was evaporated under reduced pressure. After 40 ml of n-hexane was added to the residue, the mixture was stirred. The formed white crystals were filtered and dried to give 1.05 g (yield: 63%) of Compound 1.

To 6 ml of isopropyl alcohol solution containing 0.30 g (0.90 mmol) of Compound 1 was added 0.105 g (0.90 mmol) of fumaric acid. The mixture was stirred at room temperature for an hour. The solvent was evaporated under reduced pressure and 10 ml of n-hexane and 5 ml of ethyl acetate were added to the residue. The mixture was then stirred at room temperature. The formed white crystals were filtered and dried to give 0.39 g (yield: 96%) of Compound 1 as the fumarate.

Melting point: 279.0°–283.6° C.

MS (EI) m/e: 333 (M+)

IR (KBr) cm$^{-1}$: 3400(br), 1643, 1571, 1412, 802, 654

NMR (DMSO-d$_6$) δ(ppm): 11.1–11.3(1H, br), 8.10(1H, d, J=1.6 Hz), 7.09(1H, d, J=1.6 Hz), 6.59(2H, s), 4.12(1H, q, J=2.2 Hz), 3.72(2H, m), 2.60(3H, s), 1.90–2.51(8H, m)

EXAMPLE 2

Endo-8-methyl-8-azabicyclo[3.2.1]oct-3-yl 4,5-dihydro-7-hydroxy-5-oxothieno[3,2-b]pyridine-6-carboxylate (Compound 2)

Compound 2 was obtained (yield: 19%) in a manner similar to Example 1 except for using tropine in place of 3α-amino-8-methyl-8-azabicyclo[3.2.1]octane. Compound 2 was then converted into the fumarate (yield: 40%) according to a similar manner to that for fumarate-formation in Example 1.

MS (EI) m/e: 334 (M+)

IR (KBr) cm$^{-1}$: 3400(br), 1640, 1622, 1563, 1483, 1455, 1359, 1242, 1026, 805, 760

NMR (DMSO-d$_6$) δ(ppm): 7.70(1H, d, J=5.3 Hz), 6.88(1H, d, J=5.3 Hz), 6.61(2H, s), 5.07(1H, m), 3.81(2H, m), 2.70(3H, s), 1.8–2.8(8H, m)

EXAMPLE 3

Endo-N-(8-methyl-8-azabicyclo[3.2.1]oct-3-yl)-4-(n-butyl)-4,5-dihydro-7-hydroxy-5-oxothieno[3,2-b]pyridine-6-carboxamide (Compound 3)

Compound 3 was obtained (yield: 63%) in a manner similar to Example 1 except for using Compound a obtained in Reference Example 1 in place of ethyl 4,5-dihydro-7-hydroxy-5-oxothieno[3,2-b]pyridine-6-carboxylate. Compound 3 was then converted into the fumarate (yield: 79%) according to a similar manner to fumarate-formation in Example 1.

Melting point: 211.6°–213.5° C.

MS (EI) m/e: 389 (M+)

IR (KBr) cm$^{-1}$: 3080(br), 1716, 1676, 1642, 1563, 1424, 1276, 1234, 1171, 803, 646

NMR (DMSO-d$_6$) δ(ppm): 17.06(1H, s), 11.39(1H, d, J=5.1 Hz), 8.57(1H, d, J=5.1 Hz), 7.81(1H, d, J=1.7 Hz), 6.95(2H, s), 4.21(3H, m), 3.89(2H, m), 2.53(3H, s), 1.92–2.89(8H, m), 1.66(2H, m), 1.40 (2H, m), 0.91(3H, t, J=7.5 Hz)

EXAMPLE 4

Endo-8-methyl-8-azabicyclo[3.2.1]oct-3-yl 4-(n-butyl)-4,5-dihydro-7-hydroxy-5-oxothieno[3,2-b]pyridine-6-carboxylate (Compound 4)

Compound 4 was obtained (yield: 99%) in a manner similar to Example 1 except for using Compound a obtained in Reference Example 1 in place of ethyl 4,5-dihydro-7-hydroxy-5-oxothieno[3,2-b]pyridine-6-carboxylate, and using tropine in place of 3α-amino-8-methyl-8-azabicyclo[3.2.1]-octane. Compound 4 was then converted into the fumarate (yield: 91%) according to a similar manner to that for fumarate-formation in Example 1.

Melting point: 179.7°–184.5° C.

MS (EI) m/e: 390 (M+)

IR (KBr) cm$^{-1}$: 3082, 1703, 1598, 1398, 1257, 1025, 782

NMR (DMSO-d$_6$) δ(ppm): 10.58(1H, br), 8.22(1H, d, J=5.6 Hz), 7.40(1H, d, J=5.6 Hz), 6.64(2H, s), 5.23 (1H, brs), 4.12(2H, t, J=7.3 Hz), 3.85(2H, m), 2.67(3H, s), 2.06–2.65(8H, m), 1.57(2H, m), 1.34 (2H, m), 0.91(3H, t, J=7.3 Hz)

EXAMPLE 5

Endo-N-(8-methyl-8-azabicyclo[3.2.1]oct-3-yl)-7-(n-butyl)-6,7-dihydro-4-hydroxy-6-oxothieno[2,3-b]pyridine-5-carboxamide (Compound 5)

Compound 5 was obtained (yield: 79%) in a manner similar to Example 1 except for using Compound b obtained in Reference Example 2 in place of ethyl 4,5-dihydro-7-hydroxy-5-oxothieno[3,2-b]pyridine-6-carboxylate. Compound 5 was then converted into the fumarate (yield: 90%) according to a similar manner to that for fumarate-formation in Example 1.

Melting point: 155.5°–158.2° C.

MS (EI) m/e: 389 (M+)

IR (KBr) cm$^{-1}$: 3180(br), 1666, 1553, 1425, 1276, 1232, 1212, 1004, 922, 647

NMR (DMSO-d$_6$) δ(ppm): 16.65(1H, s), 10.89(1H, d, J=6.7 Hz), 7.42(1H, d, J=5.5 Hz), 7.34(1H, d, J=5.5 Hz), 6.64(2H, s), 4.06–4.18(3H, m), 3.89(2H, m), 2.69(3H, s), 2.01–2.66(8H, m), 1.70(2H, m), 1.37 (2H, m), 0.93(3H, t, J=7.3 Hz)

EXAMPLE 6

Endo-8-methyl-8-azabicyclo[3.2.1]oct-3-yl 7-(n-butyl)-6,7-dihydro-4-hydroxy-6-oxothieno[2,3-b]pyridine-5-carboxylate (Compound 6)

Compound 6 was obtained (yield: 86%) in a manner similar to Example 1 except for using Compound b obtained in Reference Example 2 in place of ethyl 4,5-dihydro-7-hydroxy-5-oxothieno[3,2-b]pyridine-6-carboxylate, and using tropine in place of 3α-amino-8-methyl-8-azabicyclo[3.2.1]octane. Compound 6 was then converted into the fumarate (yield: 87%) according to a similar manner to that for fumarate-formation in Example 1.

Melting point: 154.4°–157.5° C.

MS (EI) m/e: 390 (M+)

IR (KBr) cm$^{-1}$: 3370(br), 1634, 1540, 1425, 1391, 1371, 1316, 1277, 1237, 1205, 1065, 1024

NMR (DMSO-d$_6$) δ(ppm): 10.58(1H, br), 7.37(1H, d, J=5.6 Hz), 7.32(1H, d, J=5.6 Hz), 6.64(2H, s), 5.23 (1H, brs), 4.01(2H, t, J=7.3 Hz), 3.86(2H, m), 2.67(3H, s), 2.05–2.65(8H, m), 1.67(2H, m), 1.35 (2H, m), 0.93(3H, t, J=7.4 Hz)

EXAMPLE 7

Endo-N-(8-methyl-8-azabicyclo[3.2.1]oct-3-yl)-6,7-dihydro-4-hydroxy-6-oxothieno[2,3-b]pyridine-5-carboxamide (Compound 7)

Compound 7 was obtained (yield: 63%) in a manner similar to Example 1 except for using ethyl 6,7-dihydro-4-hydroxy-6-oxothieno[2,3-b]pyridine-5-carboxylate [J. Chem. Res. (S), 214 (1985); J. Chem. Res. (M), 2501 (1985)] in place of ethyl 4,5-dihydro-7-hydroxy-5-oxothieno[3,2-b]-pyridine-6-carboxylate. Compound 7 was then converted into the fumarate (yield: 90%) according to a similar manner to that for fumarate-formation in Example 1.

Melting point: 296.9°–298.2° C.

MS (EI) m/e: 333 (M+)

IR (KBr) cm$^{-1}$: 1651, 1546, 1531, 1444, 1359, 1246, 805, 777, 675, 663, 561, 468

NMR (DMSO-d$_6$) δ(ppm): 7.08–7.20(2H, m), 6.55(2H, s), 4.12(1H, m), 3.72(2H, m), 2.61(3H, s), 2.00–2.69 (6H, m), 1.88–1.93(2H, m)

EXAMPLE 8

Endo-8-methyl-8-azabicyclo[3.2.1]oct-3-yl 6,7-dihydro-4-hydroxy-6-oxothieno[2,3-b]pyridine-5-carboxylate (Compound 8)

Compound 8 was obtained (yield: 66%) in a manner similar to Example 1 except for using ethyl 6,7-dihydro-4-hydroxy-6-oxothieno[2,3-b]pyridine-5-carboxylate in place of ethyl 4,5-dihydro-7-hydroxy-5-oxothieno[3,2-b]pyridine-6-carboxylate, and using tropine in place of 3α-amino-8-methyl-8-azabicyclo[3.2.1]octane. Compound 8 was then converted into the fumarate (yield: 84%) according to a similar manner to that for fumarate-formation in Example 1.

Melting point: 194.4°–197.6° C.

MS (EI) m/e: 334 (M+)

IR (KBr) cm$^{-1}$: 1637, 1541, 1416, 1384, 1323, 1230, 1191, 1026, 823, 666, 558

NMR (DMSO-d$_6$) δ(ppm) : 7.05–7.20(2H, m), 6.57(2H, s), 5.16(1H, m), 3.79(2H, m), 2.64(3H, s), 2.00–2.67 (6H, m), 1.80–1.86(2H, m)

EXAMPLE 9

Endo-N-(9-methyl-9-azabicyclo[3.3.1]non-3-yl)-6,7-dihydro-4-hydroxy-6-oxothieno[2,3-b]pyridine-5-carboxamide (Compound 9)

Compound 9 was obtained (yield: 68%) in a manner similar to Example 1 except for using ethyl 6,7-dihydro-4-hydroxy-6-oxothieno[2,3-b]pyridine-5-carboxylate in place of 4,5-dihydro-7-hydroxy-5-oxothieno[3,2-b]pyridine-6-carboxylate, and using 3α-amino-9-methyl-9-azabicyclo[3.3.1]nonane [Japanese Published Unexamined Patent Application No. 67284/1984] in place of 3α-amino-8-methyl-8-azabicyclo[3.2.1]octane. Compound 9 was then converted into the furmarate (yield: 77%) according to a similar manner to that for fumarate-formation in Example 1.

Melting point: 237.4°–240.8° C.

MS (EI) m/e: 347 (M+)

IR (KBr) cm$^{-1}$: 1664, 1419, 1276, 1231, 1007, 927, 648

NMR (DMSO-d$_6$) δ(ppm): 7.13–7.25(2H, m), 6.62(2H, s), 4.03(1H, q, J=6.9 Hz), 3.53–3.61(2H, m), 2.79(3H, s), 2.50–2.61(4H, m), 1.81–2.09(4H, m), 1.67–1.76 (2H, m)

EXAMPLE 10

Tablet

A tablet having the following ingredients is prepared in a conventional manner.

| Compound 1 | 10 mg |
| --- | --- |
| Lactose | 30 mg |
| Potato starch | 15 mg |
| Polyvinyl alcohol | 1.5 mg |
| Magnesium stearate | 0.5 mg |

EXAMPLE 11

Capsule

A capsule having the following ingredients is prepared in a conventional manner.

| Compound 1 | 10 mg |
| --- | --- |
| Lactose | 100 mg |
| Magnesium stearate | 2.5 mg |

These ingredients are blended and the mixture is filled in a gelatin capsule.

EXAMPLE 12

Injection

Injection preparation having the following ingredients is prepared in a conventional manner.

| Compound 1 | 10 mg |
| --- | --- |
| Sodium chloride | 20 mg |

These ingredients are added to water until the whole volume is 5 ml (corresponding to 1 ampoule).

Water is previously distilled and sterilized in an autoclave.

REFERENCE EXAMPLE 1

Ethyl 4-(n-butyl-4,5-dihydro-7-hydroxy-5-oxothieno[3,2-b]-pyridine-6-carboxylate (Compound a)

A) 34.1 ml (0.300 mol) of n-butyl iodide was added to a solution of 15.7 g (0.100 mol) of methyl 3-aminothiophene-2-carboxylate and 15.2 g (0.110 mol) of potassium carbonate in 200 ml of N,N-dimethylformamide at 25° C., and the mixture was stirred at 120° C. for 10 hours. After cooling, the solvent was evaporated under reduced pressure and 200 ml of ethyl acetate was added to the residue to remove inorganic salts by filtration. The filtrate was again concentrated under reduced pressure. The residue was purified by silica gel column chromatography (eluting solvent: ethyl acetate/n-hexane=1/9 v/v) to give 10.2 g (yield: 48%) of methyl 3-(n-butyl-)aminothiophene-2-carboxylate (Compound a-1)

NMR (CDCl$_3$) δ(ppm): 7.35(1H, d, J=5.3 Hz), 7.01–7.30 (1H, br), 6.98(1H, d, J=5.3 Hz), 3.83(3H, s), 3.28(2H, m), 1.21–1.88(4H, m), 0.95(3H, t, J=7.5 Hz)

B) 10.0 g (46.9 mmols) of Compound a-1 was dissolved in a solvent mixture of 90 ml of 1,2-dichloroethane and 9 ml of 1,4-dioxane. Then 16.9 ml (0.141 mol) of trichloromethyl chloroformate was dropwise added to the solution at 25° C. and the mixture was stirred at 75° C. for 7 hours. After cooling, 0.50 g of activated carbon was added to the mixture followed by reflux for an hour in a nitrogen flow. After cooling, the activated carbon was removed by filtration and the filtrate was concentrated under reduced pressure. To the residue were added 15 ml of ethyl acetate and 50 ml of n-hexane. The mixture was again stirred. The precipitated white crystals were filtered and dried to give 6.96 g (yield: 66%) of 4-(n-butyl)-5H-thieno[3,2-d]oxazine-5,7(4H)-dione (Compound a-2).

NMR (CDCl$_3$) δ(ppm): 7.95(1H, d, J=5.0 Hz), 6.97(1H, d, J=5.0 Hz), 4.01(2H, t, J=7.2 Hz), 1.17–1.98(4H, m), 0.98(3H, t, J=7.4 Hz)

C) Under ice cooling, 552 mg (24.0 mmols) of sodium hydride was added to 67.4 ml (0.444 mol) of ethyl malonate and the mixture was stirred at 25° C. for 30 minutes. 5.00 g (22.2 mmols) of Compound a-2 was added to the solution mixture, and the mixture was stirred at 150° C. for an hour. After cooling, 300 ml of water was added to the mixture, and the mixture was washed twice with chloroform. 6N Hydrochloric acid aqueous solution was added to the aqueous layer. The precipitated crystals were filtered and dried to give 3.33 g (yield: 51%) of Compound a.

NMR (CDCl$_3$) δ(ppm): 7.69(1H, d, J=5.0 Hz), 7.02(1H, d, J=5.0 Hz), 4.18(2H, q, J=7.0 Hz), 3.64(2H, t, j=7.5 Hz), 1.08–1.76(4H, m), 1.22(3H, t, J=7.0 Hz), 0.91(3H, t, J=6.1 Hz)

REFERENCE EXAMPLE 2

Ethyl 7-(n-butyl)-6,7-dihydro-4-hydroxy-6-oxothieno[2,3-b]-pyridine-5-carboxylate (Compound b)

A) Methyl 2-(n-butyl)amino-3-thiophenecarboxylate (Compound b-1) was obtained (yield: 23%) in a manner similar to Reference Example 1,A) step except for using methyl 2-aminothiophene-3-carboxylate [Chem. Ber., 98, 3571 (1965)] in place of methyl 3-aminothiophene-2-carboxylate.

NMR (CDCl$_3$) δ(ppm): 7.08–7.36(1H, br), 7.03(1H, d, J=5.5 Hz), 6.14(1H, d, J=5.5 Hz), 3.83(3H, s), 3.23 (2H, q, J=6.2 Hz), 1.22–1.90(4H, m), 0.96(3H, t, J=7.4 Hz)

B) 7-(n-Butyl)-6H-thieno[2,3-d]oxazine-4,6(7H)-dione (Compound b-2) was obtained (yield: 80%) in a manner similar to Reference Example 1,B) step except for using Compound b-1 in place of Compound a-1.

NMR (CDCl$_3$) δ(ppm): 7.59(1H, d, J=5.2 Hz), 6.30(1H, d, J=5.2 Hz), 3.97(2H, t, J=7.0 Hz), 1.15–1.93(4H, m), 0.96(3H, t, J=7.4 Hz)

C) Compound b was obtained (yield: 92%) in a manner similar to Reference Example 1,C) step except for using Compound b-2 in place of Compound a-2.

NMR (DMSO-d$_6$) δ(ppm): 7.34(1H, d, J=5.7 Hz), 7.29(1H, d, J=5.7 Hz), 4.32(2H, q, J=7.0 Hz), 3.97(2H, t, J=7.3 Hz), 1.60–1.71(2H, m), 1.30(3H, t, J=7.1 Hz), 1.26–1.40(2H, m), 0.92(3H, t, J=7.3 Hz)

What is claimed is:

1. A thienopyridine derivative represented by formula (I):

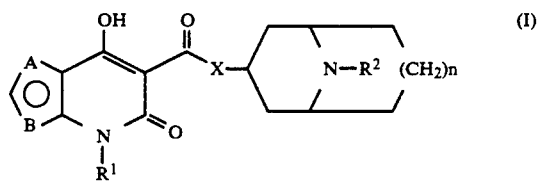

wherein one of A and B represents —S—, the other represents —CH=, X represents —O— or —NH—; $R^1$ represents hydrogen or lower alkyl; $R^2$ represents lower alkyl; and n represents 0 or 1; or a pharmaceutically acceptable salt thereof.

2. The compound according to claim 1, wherein the lower alkyl is a straight or branched alkyl having 1 to 6 carbon atoms.

3. The compound according to claim 1, wherein A represents —S—; B represents —CH=; X represents —NH—, and n is 0.

4. Endo-N-(8-methyl-8-azabicyclo[3.2.1]oct-3-yl)-4.5-dihydro-7-hydroxy-5-oxothieno[3,2-b]pyridine-6-carboxamide or a pharmaceutically acceptable salt thereof.

5. A pharmaceutical composition comprising a pharmaceutical carrier and as an active ingredient, an effective amount to treat 5-HT$_3$ antagonist mediated disorders in mammals of the compound as defined by claim 1.

* * * * *